United States Patent
Bartels et al.

(10) Patent No.: US 11,529,112 B2
(45) Date of Patent: Dec. 20, 2022

(54) X-RAY IMAGING DATA PROCESSING DEVICE AND METHOD

(71) Applicant: KONINKLIJKE PHILIPS N.V., Eindhoven (NL)

(72) Inventors: Mattias Bartels, Nordhorn (DE); Thomas Koehler, Norderstedt (DE); Ewald Roessl, Ellerau (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 192 days.

(21) Appl. No.: 16/322,509

(22) PCT Filed: Mar. 23, 2018

(86) PCT No.: PCT/EP2018/057391
§ 371 (c)(1),
(2) Date: Feb. 1, 2019

(87) PCT Pub. No.: WO2018/172501
PCT Pub. Date: Sep. 27, 2018

(65) Prior Publication Data
US 2021/0321970 A1 Oct. 21, 2021

(30) Foreign Application Priority Data
Mar. 23, 2017 (EP) .................................... 17162475

(51) Int. Cl.
*A61B 6/00* (2006.01)

(52) U.S. Cl.
CPC ............ *A61B 6/5264* (2013.01); *A61B 6/482* (2013.01); *A61B 6/484* (2013.01); *A61B 6/583* (2013.01)

(58) Field of Classification Search
CPC ......... A61B 6/583; A61B 6/484; A61B 6/482; A61B 6/5264; A61B 6/502; A61B 6/4241;
(Continued)

(56) References Cited

U.S. PATENT DOCUMENTS

| | | | |
|---|---|---|---|
| 7,646,843 B2 | 1/2010 | Popescu | |
| 7,924,973 B2 | 4/2011 | Kottler | |

(Continued)

FOREIGN PATENT DOCUMENTS

| | | |
|---|---|---|
| CN | 104970815 A | 10/2015 |
| DE | 102014213817 A1 | 6/2015 |

(Continued)

OTHER PUBLICATIONS

Epple F. et al., Phase Unwrapping in Spectral X Ray Differential Phase-Contrast Imaging With an Energy-Resolving Photon-Counting Pixel Detector, IEEE Transactions On Medical Imaging, vol. 34, No. 3, pp. 816-823, 2015.

(Continued)

*Primary Examiner* — Irakli Kiknadze
(74) *Attorney, Agent, or Firm* — Larry Liberchuk

(57) ABSTRACT

Data in X-ray images of a medical device is processed in order to reduce vibration artifacts in differential phase contrast imaging. A proportionality factor between an object induced phase shift for a first x-ray energy bin and an object induced phase shift for a second x-ray energy bin is provided. At least one of a dark field signal and an object induced phase shift is determined from a detected intensity value of a pixel for the first energy bin and a detected intensity value of the pixel for the second energy bin using the proportionality factor.

11 Claims, 1 Drawing Sheet

(58) Field of Classification Search
CPC ......... A61B 6/4035; A61B 6/06; A61B 6/542;
A61B 6/5205; A61B 6/4064; A61B
6/032; A61B 6/027; A61B 6/4291; A61B
6/035; A61B 6/4014; A61B 6/4021; A61B
6/405; A61B 6/425; A61B 6/481; A61B
6/5258; A61B 6/5211; A61B 6/107; A61B
6/5282; A61B 6/4042; A61B 6/4233;
A61B 6/463; A61B 6/4266; A61B
6/4441; A61B 6/4208; G21K 1/06; G21K
2207/005; G06T 11/003; G06T 11/005;
G06T 5/50; G06T 3/4038; G06T
2211/408; G06T 2207/20221; G06T
2207/10116; G01N 23/041; G01N 23/04;
G01N 2223/423; G01N 2223/401; G01N
23/20075; G03B 35/08; G03B 42/02
USPC .......................................................... 378/62
See application file for complete search history.

(56) References Cited

U.S. PATENT DOCUMENTS

| 8,155,422 | B2 | 4/2012 | Ziegler |
| 9,538,970 | B2 | 1/2017 | Koehler |
| 9,907,524 | B2 | 3/2018 | Baturin |
| 2014/0185746 | A1 | 7/2014 | Baturin |
| 2016/0242726 | A1 | 8/2016 | Koehler |
| 2018/0228455 | A1* | 8/2018 | Koehler ............... A61B 6/4241 |

FOREIGN PATENT DOCUMENTS

| WO | WO2014100063 | A1 | 6/2014 |
| WO | WO2016177903 | A1 | 11/2016 |

OTHER PUBLICATIONS

Koehler, T. et al., "Slit-Scanning Differential X-Ray Phase-Contrast Mammography: Proof-of-Concept Experimental Studies", Medical Physics, vol. 42, Issue 4, pp. 1959-1965, Apr. 2015.

* cited by examiner

X-RAY IMAGING DATA PROCESSING DEVICE AND METHOD

FIELD OF THE INVENTION

The invention is related to processing x-ray imaging data, in particular phase contrast x-ray imaging data.

BACKGROUND OF THE INVENTION

Grating-based differential phase contrast imaging has gained increased momentum in recent years. Such technique is capable of delivering additional information, which is complementary to the conventional attenuation image, namely refraction and dark-field signals. Among others, full field digital mammography (FFDM) is a promising application of this technology. Recently, the first clinical FFDM unit was successfully equipped with x-ray grating hardware based on the Philips MicroDose L30 (see, T. Koehler et al., Slit-scanning differential x-ray phase-contrast mammography: Proof-of-concept experimental studies, Medical Physics 42, 1959 (2015)). First results demonstrate that the slit-scanning systems meet relevant requirements with respect to FOV, scan time, and dose.

Differential phase contrast imaging, however, is susceptible to mechanical instabilities and vibrations. In order to extract the object parameters (attenuation, refraction and dark-field signal) the recorded data is typically processed by taking into account a reference scan without object ("blank scan", see the article by T. Koehler et al, cited above). Consequently, the resulting image quality is limited by the repeatability of the Moiré pattern obtained during repeated scans. Conventionally, deviations induced, for example, by vibration between blank scan and object scan are erroneously attributed to the object and result in image artifacts.

There are attempts, as discussed for example, in DE 102014213817 A1, which aim at reducing the occurrence of vibrations and the like by means of structural modifications to the imaging arrangement. However, such structural modifications result in more complicated machinery, i.e. higher costs, while even sophisticated attempts may not completely eliminate undesired influences.

SUMMARY OF THE INVENTION

It is an object of the present invention to provide an approach for addressing the aforementioned problems associated with vibrations and the like in, in particular, grating-based differential phase contrast imaging.

In a first aspect of the present invention a processing device for energy-binned differential phase contrast x-ray imaging data is presented comprising a proportionality factor providing unit arranged to provide a proportionality factor between an object induced phase shift for a first x-ray energy bin and an object induced phase shift for a second x-ray energy bin, and a dark field and phase shift determining unit arranged to determine at least one of a dark field signal and an object induced phase shift from a detected intensity value, included in the imaging data, of a pixel for the first energy bin and a detected intensity value of the pixel for the second energy bin, using the proportionality factor provided by the proportionality factor providing unit. In the context of the claimed invention the term 'dark field and phase shift determination unit' may also mean a single unit that is arranged to both determine a dark field signal and an object induced phase shift or a determination unit that is arranged to determine a dark field signal and an object induced phase shift individually in separate sub-units.

In a second aspect of the present invention a proportionality factor determination device for determining a proportionality factor between an object induced phase shift for a first x-ray energy bin and an object induced phase shift for a second x-ray energy bin in the context of energy-binned differential phase contrast x-ray imaging is presented comprising a calculation unit arranged to calculate a first phase shift for the first energy bin from a phase image obtained by differential phase contrast x-ray imaging, using the first energy bin, a phantom having a predetermined shape and to calculate a second phase shift for the second energy bin from a phase image obtained by differential phase contrast x-ray imaging, using the second energy bin, the phantom, and an obtaining unit arranged to obtain the proportionality factor from the first phase shift and the second phase shift.

In a third aspect of the present invention a processing method for energy-binned differential phase contrast x-ray imaging data is presented comprising a proportionality factor providing step of providing a proportionality factor between an object induced phase shift for a first x-ray energy bin and an object induced phase shift for a second x-ray energy bin, and a determining step of determining at least one of a dark field signal and an object induced phase shift from a detected intensity value, included in the imaging data, of a pixel for the first energy bin and a detected intensity value of the pixel for the second energy bin, using the proportionality factor provided by the proportionality factor providing step.

In a fourth aspect of the present invention a proportionality factor determination method for determining a proportionality factor between an object induced phase shift for a first x-ray energy bin and an object induced phase shift for a second x-ray energy bin in the context of energy-binned differential phase contrast x-ray imaging is presented, comprising a calculation step of calculating a first phase shift for the first energy bin from a phase image obtained by differential phase contrast x-ray imaging, using the first energy bin, a phantom having a predetermined shape and calculating a second phase shift for the second energy bin from a phase image obtained by differential phase contrast x-ray imaging, using the second energy bin, the phantom, and an obtaining step of obtaining the proportionality factor from the first phase shift and the second phase shift.

The invention addresses the problems associated, for example, with vibrations in grating-based differential phase contrast imaging by making use of spectral information. It was realized by the inventors, that one may make use of the spectral information in determining the vibration state of the Moiré pattern based on multi-energy-bin x-ray detectors, the energy independence of vibration-induced Moiré pattern phase shifts, the energy dependence of object-induced Moiré pattern phase shifts and a phantom designed to allow for measuring the dependence of the object-induced phase shift as a function of the energy bin.

In particular, it was found that by suitable data processing the vibration-induced shifts and the like can be disentangled from the object properties and hence vibration artifacts in the image are reduced, while there is no particular need for changing the basic physical structure of the imaging device.

It is noted here that the invention is not limited to the case of just two energy bins, as more than two energy bins are also contemplated. When considering the respective detected intensity values, three or even more energy bins may be used for determining the phase shift due to vibration, while the use of further energy bins gives the benefit of allowing for separate (somewhat independent) determinations, e.g. by considering the first and the second energy bin, considering the first and a (further) third energy bin and considering the second and the third energy bin, respectively, as discussed herein explicitly for just two energy bins. Also, two energy bins may be used for identifying the phase shift due to the vibration, which is then used for compensation in a simultaneous differential phase contrast imaging using the third energy bin.

In a preferred embodiment, the proportionality factor providing unit is arranged to provide the proportionality factor depending on an attenuation value for the first energy bin and an attenuation value for the second energy bin.

In providing the proportionality factor in dependence from the attenuation values of the first and second energy bin, respectively, an increase accuracy is achievable, while depending on the circumstances it may be possible to provide just an approximation of the factor, which is not changing for different attenuations (e.g. in case there is only little influence).

In a preferred modification of the above embodiment, the proportionality factor providing unit includes a look-up table.

A look-up table allows a quick access to the proportionality factor by using the attenuation values as parameters for the looking up. Nevertheless, also other ways of providing the factor are possible, e.g. providing an equation for calculating or a combination of calculation and look-up table.

In a preferred embodiment, the dark field signal and phase shift determining unit is arranged to determine, from measured data $m_{i,1}$ of the first energy bin and measured data $m_{i,2}$ of the second energy bin, an attenuation value $A_1$ for the first energy bin, an attenuation value $A_2$ for the second energy bin, a dark field signal $D_1$ for the first energy bin, a dark field signal $D_2$ for the second energy bin, an object induced phase shift $\phi_1$ and a disturbance induced phase shift $\psi_i$ in such way that a likelihood obtaining the measured data is maximized for the selected image values.

This includes, for example, that a cost function that penalizes differences between measured data and expected data is minimized.

In a preferred modification of the above embodiment, the dark field signal and phase shift determining unit is arranged to employ a least square minimization according to $$\Delta(A_1,A_2,D_1,D_2,\phi_1,\psi_i)=\Sigma(m_{i,1}A_1B_{i,1}(1+D_1V_{i,1}\cos(\alpha_{i,1}+\psi_i+\phi_1)))^2+$$

$$\Sigma(m_{i,2}-A_2B_{i,2}(1+D_2V_{i,2}\cos(\alpha_{i,2}+\psi_i+c\cdot\phi_1)))^2,$$

with $B_{i,1}$, $B_{i,2}$, $V_{i,1}$, $V_{i,2}$, $\alpha_{i,1}$, and $\alpha_{i,2}$ being the intensity, the visibility and the phase of a Moiré pattern obtained during a blank scan, respectively.

Using an approach like least square minimization, however, is just one option. As in the given situation, one deals with photon counting, minimizing a negative Poisson log-likelihood, if the blank scan intensities vary, one might also want to use a weighted least squares cost function.

In a further preferred embodiment, which may specifically considered also as a preferred modification of the above embodiment, the dark field signal and phase shift determining unit is arranged to include, in the determination (e.g. in the least square minimization), a further limitation as to favor small differences between disturbance induced phase shifts of neighboring pixels. In particular, specifically in the context of the least square minimization, this might correspond to a limitation as to the absolute difference between disturbance induced phase shifts of neighboring pixels being less than a predetermined value.

It may be considered as a priori knowledge that neighboring pixels would suffer from similar disturbance or vibration, so that such information may be included in the determination. It may be noted that vibrations may change the relative position of the gratings with respect to each other, wherein furthermore the interferometer may be quite sensitive to such changes (it was found that even changes in a μm range may create a visible effect).

In a preferred embodiment, a proportionality factor determination system for determining a proportionality factor between an object induced phase shift for a first x-ray energy bin and an object induced phase shift for a second x-ray energy bin in the context of energy-binned differential phase contrast x-ray imaging is provided and comprises a proportionality factor determination device according to the present invention, and a phantom, wherein the phantom includes a plurality of portions, each portion having a height changing in a direction transverse to a beam direction of the x-ray in predetermined manner, the height of the portions of the phantom being the extension of the portions in the beam direction, wherein different portions of the phantom have different average heights, wherein the proportionality factor determination device is arranged to determine the proportionality factor depending on an attenuation value for the first energy bin and an attenuation value for the second energy bin.

In a preferred embodiment, a differential phase contrast x-ray imaging system is provided and comprises a differential phase contrast imaging unit, an x-ray source arranged to provide x-rays of a first and a second energy bin, the processing device according to the present invention arranged to receive energy-binned differential phase contrast x-ray imaging data from the differential phase contrast imaging.

In a preferred modification of the above embodiment, the imaging system further comprises the proportionality factor determination system according to the above embodiment, wherein the proportionality factor determination system is arranged to provide information on the proportionality factor to the proportionality factor providing unit of the processing device.

Cases are contemplated where the proportionality factor may be constant (or at least sufficiently approximated by a constant value (or set of values)), so that no specific arrangement would be needed for determining the value (other than means for storing a predetermined value or set of value), while in other cases, the proportionality factor determination system, arranged for specifically determining the information on the proportionality factor, is advantageous, for instance in a case when the energy bin size is so large that the effective energy measured by these bins is significantly changed due to beam-hardening by the object. However, for narrow energy bins, it may be sufficient to use simply equation (5) (see below) to calculate the proportionality factor.

In further aspects of the present invention a software product for processing method for energy-binned differential phase contrast x-ray imaging data, the software product comprising program code means for causing a computer to carry out the steps of a method according to the invention when the software product is run on the computer and a software product for determining a proportionality factor between an object induced phase shift for a first x-ray energy bin and an object induced phase shift for a second x-ray energy bin in the context of energy-binned differential phase contrast x-ray imaging, the software product comprising program code means for causing a computer to carry out the steps of a method according to the invention when the software product is run on the computer are presented It shall be understood that the processing device of claim 1, the determination unit of claim 7, the processing method of claim 11, the determination method of claim 12, and the computer programs of claims 13 and 14 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
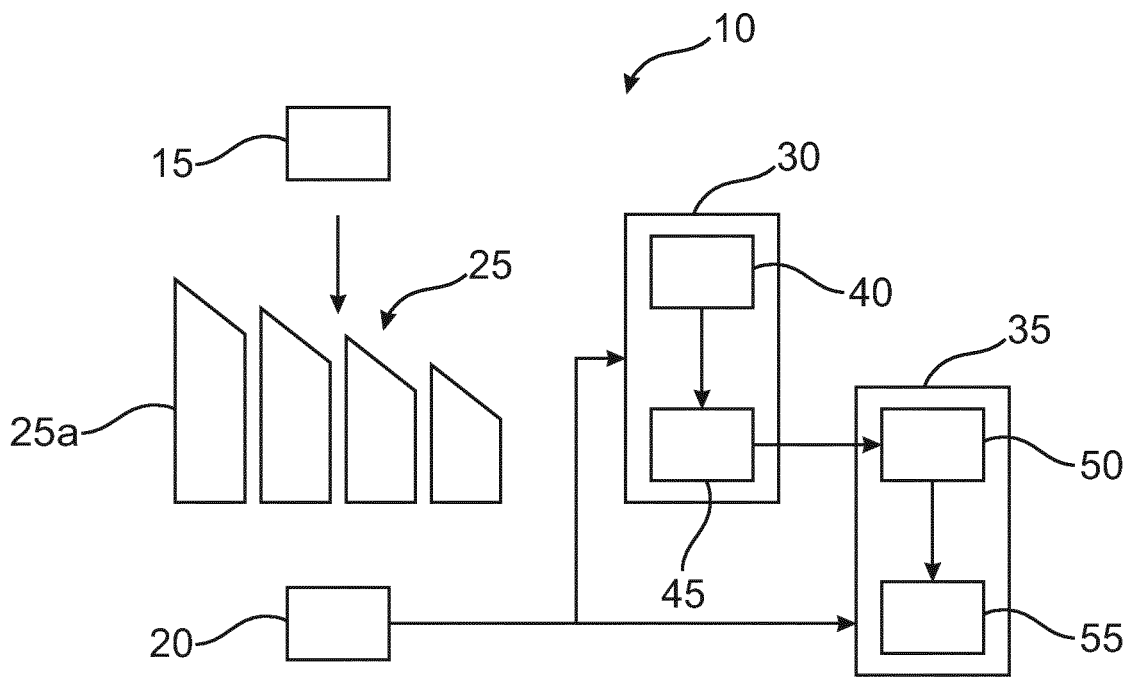
FIG. 1 shows a differential phase contrast x-ray imaging system in accordance with an embodiment of the invention.

FIG. 1 shows a differential phase contrast x-ray imaging system in accordance with an embodiment of the invention.

The system 10 includes an x-ray source 15 arranged to provide x-rays of a first and a second energy bin, e.g. including photons of a first energy range and photons of a second energy range and a corresponding differential phase contrast imaging unit 20.

In FIG. 1, between the x-ray source 15 and the imaging unit 20, a phantom 25 is provided, while, in operation of the system 10 for imaging an object, the object (not shown) rather than the phantom 25 is provided between the x-ray source 15 and the imaging unit 20.

The phantom 25 consists of several pillars 25a of different height. On top of these pillars 25a are triangles with constant slope of projected material height in beam direction. It is noted that a constant gradient of projected electron density (realized by material height in beam direction) produces a constant phase shift of the Moiré pattern.

Further, in the system 10, the imaging unit 20 is coupled to a proportionality factor determination device 30 and a processing device 35.

The proportionality factor determination device 30 includes a calculation unit 40 and an obtaining unit 45, the operation of which is discussed below.

The processing unit 35 includes a proportionality factor providing unit 50 and a dark field signal and phase shift determining unit 55, the operation of which becomes also clear from the discussion below.

The proportionality factor providing unit 50 is coupled to the proportionality factor determination device 30 to receive data or information on the proportionality factor therefrom.

Figure 2:
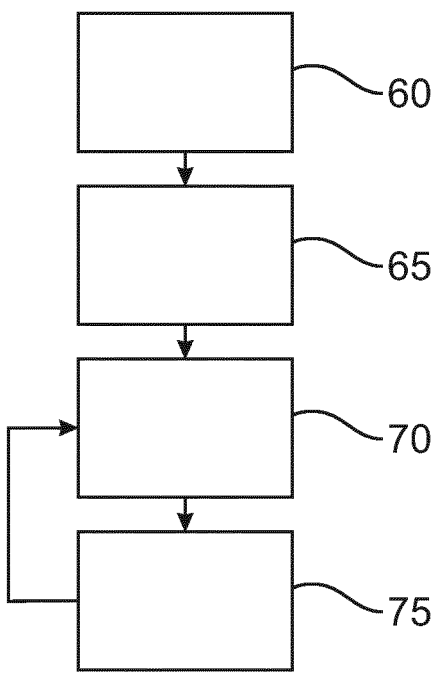
FIG. 2 shows a flow diagram illustrating a processing method for energy-binned differential phase contrast x-ray imaging data in accordance with an embodiment of the invention.

FIG. 2 shows a flow diagram illustrating a processing method for energy-binned differential phase contrast x-ray imaging data in accordance with an embodiment of the invention.

As additionally also discussed below, the method of this embodiment includes a calculation step 60, in which a first phase shift for the first energy bin is calculated from a phase image, which is obtained by differential phase contrast x-ray imaging a phantom as shown in FIG. 1, wherein the phase image uses or corresponds to the first energy bin. The calculation step 60 also includes calculating a second phase shift for the second energy bin from a phase image obtained by differential phase contrast x-ray imaging the phantom, here using the second energy bin.

Based on the information calculated in the calculation step 60, a following obtaining step 65 includes obtaining the proportionality factor from the first phase shift and the second phase shift, while additionally the influence as to the attenuation is taken into consideration, based on the phantom.

The obtained proportionality factor is provided, in a proportionality factor providing step 70, and indicates the proportionality between an object induced phase shift for a first x-ray energy bin and an object induced phase shift for a second x-ray energy bin.

Eventually, a determining step 75 is provided of determining at least one of a dark field signal and an object induced phase shift from a detected intensity value, included in the imaging data, of a pixel for the first energy bin and a detected intensity value of the pixel for the second energy bin, using the proportionality factor provided by the proportionality factor providing step 70.

In the following, the above outline of the embodiments of the invention is further discussed.

A commonly employed model for the intensity measured behind a Talbot-Lau interferometer for pixel i of a common geometrical ray is $$I_i = AB_i(1 + DV_i \cos(\alpha_i + \phi))), \quad (1)$$

where $B_i$, $V_i$ and $\alpha_i$ denote the intensity, the visibility, and the phase of the Moiré pattern obtained during a blank scan, respectively. The object parameters A, D and $\phi$ correspond to attenuation, dark field signal, and phase shift, respectively. The object parameters are obtained by least square minimization using the measured data $m_i$ $$\Delta(A,D,\phi) = \Sigma(m_i - AB_i(1 + DV_i \cos(\alpha_i + \phi)))^2 \quad (2)$$

However, as indicated above, mechanical vibrations produce additional phase shifts $\psi_i$ of the Moiré pattern corresponding to $$I_i = AB_i(1 + DV_i \cos(\alpha_i + \psi_i + \phi)). \quad (3)$$

With non-spectral data accumulation $\phi$ and $\psi_i$ cannot be separated during minimization. However, using an x-ray detector with two energy bins e=[1,2], equation (3) reads $$I_{i,e} = A_e B_{i,e}(1 + D_e V_{i,e} \cos(\alpha_{i,e} + \psi_i + \phi_e)). \quad (4)$$

It is noted that all parameters depend on photon energy, except the vibration shift $\psi_i$.

For mono energetic x-ray photons the energy dependence of the phase shift $\phi$ yields $$\phi(E_2) = \phi(E_1)\frac{E_1^2}{E_2^2}. \quad (5)$$

For polychromatic x-rays the proportionality factor c describes the relation between the phase shifts $\phi_1$ and $\phi_2$ obtained in both energy bins via $$\phi_1 = c(s_1, s_2) \cdot \phi_2 \quad (6)$$

and depends on the effective energy spectra $s_1$ and $s_2$ corresponding to both energy bins. It can be measured using a phantom sketched in FIG. 1.

Using equation (2) separately for both energy bins yields phase images for both bins. By averaging over the area corresponding to individual pillars in the phase images one obtains c for each pillar via equation (6). Due to different heights the pillars produce different degrees of beam hardening which is encoded in the attenuation signal for both bins $A_1$, $A_2$ which can be extracted from the attenuation images. Following this strategy one may obtain a look-up-table for $c(A_1, A_2)$.

In a slightly different embodiment (not illustrated), the proportionality factor c is equaled, similar to the case of mono energetic x-ray photons, also for polychromatic x-rays as corresponding to the quotient of the mean energies of the energy bins, while correspondingly also such look-up table for $c(A_1, A_2)$ may be obtained.

In order to disentangle vibration-induced shifts from object parameters we explicitly write equation (3) for both energy bins and make use of equation (6).

$$I_{i,1} = A_1 B_{i,1}(1 + D_1 V_{i,1} \cos(\alpha_{i,1} + \psi_i + \phi_1)). \quad (7)$$

$$I_{i,2} = A_2 B_{i,2}(1 + D_2 V_{i,2} \cos(\alpha_{i,2} + \psi_i + c(A_1, A_2) \cdot \phi_1)). \quad (8)$$

By least square minimization using the measured data $m_{i,e}$ from both bins the object phase $\phi_1$ can be disentangled from the vibrational component $\psi_i$:

$$\Delta(A_1, A_2, D_1, D_2, \phi_1, \psi_i) = \Sigma(m_{i,1} - A_1 B_{i,1}(1 + D_1 V_{i,1} \cos(\alpha_{i,1} + \psi_i + \phi_1)))^2 +$$

$$\Sigma(m_{i,2} - A_2 B_{i,2}(1 + D_2 V_{i,2} \cos(\alpha_{i,2} + \psi_i + c \cdot \phi_1)))^2 \quad (9)$$

It is noted that the above provides already sufficient information to separate between object induced phase shift and vibration induced phase shift on a per-pixel basis. However, the estimate can be made even more robust by adding some further prior knowledge, namely that the vibration induced phase should be the same (or almost the same) for neighboring pixels if the data are acquired simultaneously with neighboring detector pixels. If pixels in a line in the image perpendicular to the scan direction are indexed by x, the minimization can be formulated as:

$$\Delta(A_1, A_2, D_1, D_2, \phi_1, \psi_i) = \Sigma_{i,x}(m_{ix,1} - A_{1x} B_{ix,1}(1 + D_{1x} V_{ix,1} \cos(\alpha_{ix,1} + \psi_{ix} + \phi_{1x})))^2 +$$

$$\Sigma_{i,x}(m_{ix,2} - A_{2x} B_{ix,2}(1 + D_{2x} V_{ix,2} \cos(\alpha_{ix,2} + \psi_{ix} + c \cdot \phi_{1x})))^2 +$$

$$\beta \Sigma_{i,x}(\psi_{i,x} - \psi_{i,x+1})^2 \quad (10)$$

where $\beta$ is a regularization parameter that controls how much variation of the vibration-induced phase is allowed. In this case, also the vibration phase of the neighboring pixel is taken into consideration. Bold symbols are used for referral to vectors. The last term favors small differences between disturbance induced phase shifts of neighboring pixels, which is in-line with the a-priori knowledge that these differences have the common cause of vibrating gratings.

It is proposed by the inventors to circumvent problems involved with mechanical instabilities and variations by making use of spectral information based on multi-energy-bin x-ray detectors. The vibrational state of the Moiré pattern can be determined by exploiting the energy independence of vibration-induced Moiré pattern phase shifts and the energy dependence of object-induced shifts. The inventors propose a phantom to measure the energy dependence of the object-induced phase shift. By suitable data processing the vibration-induced shifts can be disentangled from the object properties to minimize image artifacts.

While the invention has been illustrated and described in detail in the drawings and foregoing description, such illustration and description are to be considered illustrative or exemplary and not restrictive; the invention is not limited to the disclosed embodiments.

In particular, it is pointed out that the above discussion refers to the use of two energy bins, while the invention is not to be understood as being limited in such way, as, for example, in case of additional energy bins, additional proportionality factors may also be provided accordingly.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single processor, device or other unit may fulfill the functions of several items recited in the claims. The mere fact that certain measures are recited in mutually different dependent claims does not indicate that a combination of these measures cannot be used to advantage.

Operations like providing, determining, calculating, obtaining, and processing can be implemented as program code means of a computer program and/or as dedicated hardware.

A computer program may be stored and/or distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A medical device for processing data in X-ray images to reduce vibration artifacts in differential phase contrast imaging, comprising:
    a processor configured to provide a proportionality factor between an object induced phase shift for a first x-ray energy bin and an object induced phase shift for a second x-ray energy bin, and
    determine at least one of a dark field signal and an object induced phase shift from a detected intensity value of a pixel for the first energy bin and a detected intensity value of the pixel for the second energy bin using the proportionality factor.

2. The medical device according to claim 1, wherein the proportionality factor is dependent on a first attenuation value for the first energy bin and a second attenuation value for the second energy bin.

3. The medical device according to claim 2, further comprising a look-up table that includes the first and second attenuation values and the proportionality factor.

4. The medical device according to claim 1, wherein first attenuation value for the first energy bin, a second attenuation value for the second energy bin, a first dark field signal for the first energy bin, a second dark field signal for the second energy bin, an object induced phase shift and a disturbance induced phase shift are determined based on measured data of the first and second energy bins in such way that a likelihood obtaining the measured data is maximized.

5. The medical device according to claim 1, wherein the processor is configured to use a least square minimization equation.

6. The medical device according to claim 1, wherein the dark field and phase shift determining unit is arranged to include, in the determination, a further limitation as to favor small differences between disturbance induced phase shifts of neighboring pixels.

7. The medical device according to claim 1, wherein the processor is further configured to:
   using the first energy bin to calculate a first phase shift for the first energy bin from a phase image obtained by differential phase contrast x-ray imaging a phantom that has a predetermined shape;
   using the second energy bin to calculate a second phase shift for the second energy bin from the phase image obtained by differential phase contrast x-ray imaging the phantom; and
   obtain the proportionality factor from the first phase shift and the second phase shift.

8. The medical device according to claim 7, wherein the phantom includes a plurality of portions, each portion having a height changing in a direction transverse to a beam direction of an X-ray, and wherein different portions of the phantom have different average heights.

9. A differential phase contrast x-ray imaging system, comprising:
   a differential phase contrast imaging unit;
   an x-ray source arranged to provide x-rays of a first and a second energy bin; and
   a medical device for processing data in X-ray images to reduce vibration artifacts in differential phase contrast imaging, comprising:
      a processor configured to provide a proportionality factor between an object induced phase shift for a first x-ray energy bin and an object induced phase shift for a second x-ray energy bin, and determine at least one of a dark field signal and an object induced phase shift from a detected intensity value of a pixel for the first energy bin and a detected intensity value of the pixel for the second energy bin using the proportionality factor.

10. A method for processing data in X-ray images of a medical device to reduce vibration artifacts in differential phase contrast imaging, comprising:
   providing a proportionality factor between an object induced phase shift for a first x-ray energy bin and an object induced phase shift for a second x-ray energy bin; and
   determining at least one of a dark field signal and an object induced phase shift from a detected intensity value of a pixel for the first energy bin and a detected intensity value of the pixel for the second energy bin using the proportionality factor.

11. The method of claim 10, further comprising:
   using the first energy bin to calculate a first phase shift for the first energy bin from a phase image obtained by differential phase contrast x-ray imaging a phantom having a predetermined shape;
   using the second energy bin to calculate a second phase shift for the second energy bin from a phase image obtained by differential phase contrast x-ray imaging the phantom; and
   obtaining the proportionality factor from the first phase shift and the second phase shift.

* * * * *